US008931637B2

(12) United States Patent
Deeds

(10) Patent No.: US 8,931,637 B2
(45) Date of Patent: Jan. 13, 2015

(54) MEDICAL LUMEN ACCESS DEVICE ASSEMBLY INCLUDING MEDICAL LUMEN ACCESS DEVICE HOLDER AND METHOD OF USE

(75) Inventor: Andrew Deeds, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 265 days.

(21) Appl. No.: 13/414,027

(22) Filed: Mar. 7, 2012

(65) Prior Publication Data

US 2012/0283667 A1    Nov. 8, 2012

Related U.S. Application Data

(60) Provisional application No. 61/482,255, filed on May 4, 2011.

(51) Int. Cl.
*B65D 83/10* (2006.01)
*A61M 25/00* (2006.01)
*A61B 19/02* (2006.01)

(52) U.S. Cl.
CPC .......... *A61M 25/002* (2013.01); *A61B 19/0256* (2013.01); *A61M 25/0097* (2013.01); *A61M 2025/0046* (2013.01)
USPC ............................ 206/364; 604/265; 604/523

(58) Field of Classification Search
CPC .................................................. A61M 25/002
USPC ........................... 604/528, 265; 206/363, 364
See application file for complete search history.

(56) References Cited

U.S. PATENT DOCUMENTS

| 5,125,416 | A | | 6/1992 | Phillips |
| 5,279,573 | A | | 1/1994 | Klosterman |
| 5,390,898 | A | * | 2/1995 | Smedley et al. ........... 251/149.6 |
| 5,443,081 | A | | 8/1995 | Klosterman |
| 5,507,300 | A | * | 4/1996 | Mukai et al. .................. 600/585 |
| 5,738,213 | A | | 4/1998 | Whiting et al. |
| 6,047,825 | A | | 4/2000 | Samuels |
| 6,547,072 | B2 | | 4/2003 | Whiting et al. |
| 6,588,588 | B2 | | 7/2003 | Samuels |
| 6,656,517 | B2 | * | 12/2003 | Michal et al. ................ 427/2.24 |
| 6,848,574 | B1 | * | 2/2005 | Israelsson et al. ............ 206/210 |
| 7,621,880 | B2 | | 11/2009 | Ryan et al. |
| 2005/0278012 | A1 | * | 12/2005 | Vonderwalde ............... 623/1.11 |

* cited by examiner

*Primary Examiner* — Laura Bouchelle
(74) *Attorney, Agent, or Firm* — Liell + McNeil

(57) ABSTRACT

A medical lumen access device assembly includes a medical lumen access device holder including an elongate tube defining a lumen extending from a proximal opening of the elongate tube to a distal opening of the elongate tube. A check valve is positioned over an opening of the elongate tube and includes a valve member having a biased closed position wherein an internal volume defined by the lumen is fluidly blocked from an exterior of the elongate tube at the opening and an open position defining a fluid path from the exterior to the internal volume through the opening. The medical lumen access device assembly also includes a medical lumen access device disposed at least partially within the lumen and having a proximal segment extending beyond the distal opening. At least a portion of the medical lumen access device includes a hydrophilic coating.

18 Claims, 3 Drawing Sheets

MEDICAL LUMEN ACCESS DEVICE ASSEMBLY INCLUDING MEDICAL LUMEN ACCESS DEVICE HOLDER AND METHOD OF USE

RELATION TO OTHER PATENT APPLICATION

This application claims priority to provisional patent application 61/482,255, filed May 4, 2011, with the same title.

TECHNICAL FIELD

The present disclosure relates generally to a medical lumen access device assembly including a medical lumen access device holder, and more particularly to a medical lumen access device holder for a medical lumen access device having a hydrophilic coating.

BACKGROUND

A variety of elongate medical devices exist that may be introduced into a patient for many different purposes. For example, elongate medical devices, such as wire guides, catheters, and the like, may be used to supply fluids, perform diagnostic or surgical procedures, implant devices, or introduce various medical instruments. These elongate medical devices may have a variety of shapes and sizes, but generally always include an elongate shaft ranging in length from several inches to several feet long, with the diameter of the shaft being much smaller than its length. Further, the elongate medical devices may include one or more lumens, and/or may have a distal end that is shaped or configured to carry out the specific medical procedure for which the device is designed. To assist in navigation of the medical device relative to the vasculature of the patient and/or other medical devices, all or a portion of the medical device may be coated with a hydrophilic coating.

These elongate medical devices may be packaged for sterilization and shipping within an elongate medical device holder. Generally, the packaging will provide protection for the medical device and ensure the sterility of the device upon delivery. According to one example, the elongate medical device holder, and thus medical device, may be provided in a spiral configuration to make the holder and device more compact for placement in a sterilization pouch and/or to conserve space when shipping and storing the device. Before use of an elongate medical device having a hydrophilic coating, a clinician will typically hydrate the hydrophilic coating by introducing a liquid, such as saline, into the medical device holder. The medical device may then remain in the medical device holder until the clinician removes the medical device from the holder prior to use. A previously unrecognized problem of the elongate medical device, having a hydrated hydrophilic coating, sticking in the medical device holder during removal, particularly if a significant period of time has lapsed between hydration and removal, has been identified.

The present disclosure is directed toward one or more of the problems set forth above.

SUMMARY OF THE DISCLOSURE

In one aspect, a medical lumen access device assembly includes a medical lumen access device holder including an elongate tube defining a lumen extending from a proximal opening of the elongate tube to a distal opening of the elongate tube. A check valve is positioned over an opening of the elongate tube and includes a valve member having a biased closed position wherein an internal volume defined by the lumen is fluidly blocked from an exterior of the elongate tube at the opening and an open position defining a fluid path from the exterior to the internal volume through the opening. The medical lumen access device assembly also includes a medical lumen access device disposed at least partially within the lumen and having a proximal segment extending beyond the distal opening. At least a portion of the medical lumen access device includes a hydrophilic coating.

In another aspect, a medical lumen access device holder includes an elongate tube defining a lumen extending from a proximal opening of the elongate tube to a distal opening of the elongate tube. A check valve is positioned over the proximal opening and includes a valve member having a biased closed position wherein an internal volume defined by the lumen is fluidly blocked from an exterior of the elongate tube at the proximal opening and an open position defining a fluid path from the exterior to the internal volume through the proximal opening. An end cap is positioned over the distal opening and defines an inwardly tapered cone-shaped channel terminating at a hole having a reduced diameter that is smaller than a diameter of the lumen.

In yet another aspect, a method of using a medical lumen access device assembly includes storing a medical lumen access device at least partially within a medical lumen access device holder. A valve member of a check valve positioned through an opening of the medical lumen access device holder is moved from a biased closed position to an open position by injecting a liquid into an internal volume of the medical lumen access device holder through the check valve. Leakage of the liquid from the internal volume to an exterior is inhibited at least in part by biasing the valve member from the open position to the biased closed position. Friction of the medical lumen access device relative to the medical lumen access device holder during removal of the medical lumen access device through a distal opening of the medical lumen access device holder is reduced with the liquid.

DETAILED DESCRIPTION

Figure 1:
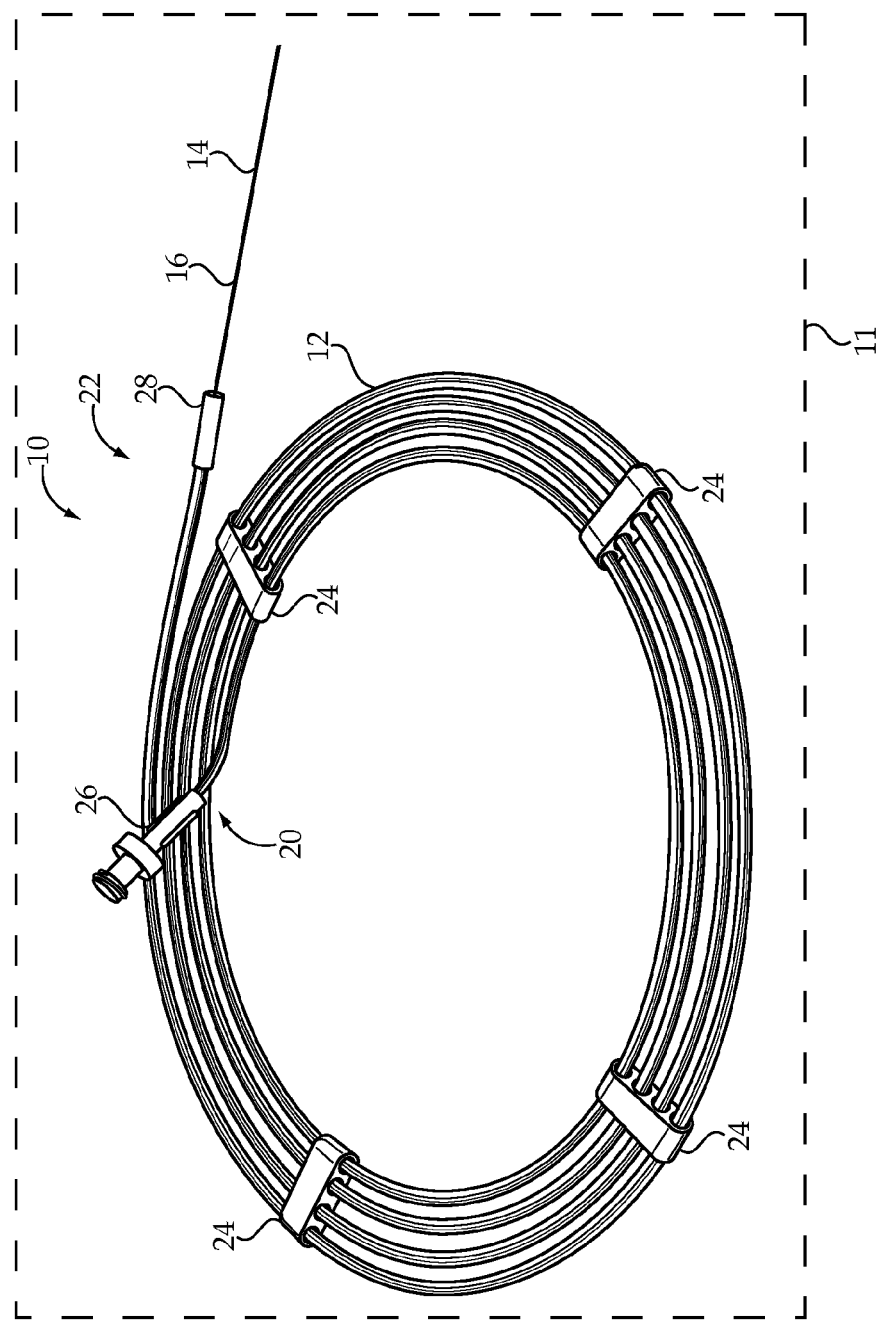
FIG. 1 is perspective view of a medical lumen access device assembly, according to the present disclosure.

Referring to FIG. 1, there is shown a medical lumen access device assembly 10 according to the present disclosure. The medical lumen access device assembly 10 generally includes a medical lumen access device holder 12 and a medical lumen access device 14 that may be stored within the medical lumen access device holder 12. The medical lumen access device 14 may include any of a variety of elongate, and sometimes hollow, medical devices that may be introduced into a patient for many different purposes. For example, the medical lumen access device 14 may be used to supply fluids, perform diagnostic or surgical procedures, implant devices, or introduce various medical instruments. Exemplary devices may include wire guides, catheters, and the like.

As should be appreciated, the medical lumen access device 14 may be made from a variety of materials and may be provided in any of a variety of shapes and sizes. Generally, the medical lumen access device 14 may include an elongate shaft ranging in length from several inches to several feet long, and may have a shaft diameter that is orders of magnitude smaller than its length. The medical lumen access device 14 may include one or more lumens extending through most or all of the length of the shaft and, further, may include a distal end that is shaped or configured to carry out a particular procedure. For example, the distal end may be curved to assist in navigating the vasculature of a patient. As should be appreciated, the medical lumen access device 14 may have both vascular and non-vascular applicability, as such devices may also be used, for example, to access bile ducts of a patient.

According to the present disclosure, at least a portion of the medical lumen access device 14 includes a hydrophilic coating 16. Hydrophilic coatings are generally known and may be provided on a surface of the medical lumen access device 14 to increase lubricity, which may ease insertion, manipulation, and removal of the medical lumen access device 14 relative to a patient and/or another medical device. As should be appreciated, the hydrophilic coating 16 may reduce friction forces that may affect accurate positioning of the medical lumen access device 14 and, potentially, cause patient discomfort.

The medical lumen access device holder 12, which may be used to store the medical lumen access device 14, includes an elongate tube 18 having a proximal end 20 and a distal end 22. As should be appreciated, the medical lumen access device holder 12 is provided as a shipping and storage device and, according to the present disclosure, is not intended for insertion into a patient. Prior to use, the assembly 10 shown in FIG. 1 may be sterile and sealed within a tear open package 11 (shown in shadow) of a type well known in the art. As shown, the elongate tube 18 may have a spiral configuration that is fixed using a plurality of separators 24 attached to the elongate tube 18 at spaced apart axial lengths of the elongate tube 18. Although a spiral configuration is shown, alternative configurations facilitating compactness of the medical lumen access device holder 12 for shipping and storage may also be used.

According to the exemplary embodiment, the medical lumen access device holder 12 may also include a check valve 26 positioned at the proximal end 20 and an end cap 28 positioned at the distal end 22. Although the exemplary embodiment includes both the check valve 26 and the end cap 28, alternative embodiments may include only one of the check valve 26 and the end cap 28. Benefits and advantages of using one or both of the check valve 26 and the end cap 28 will be discussed below.

Figure 2:
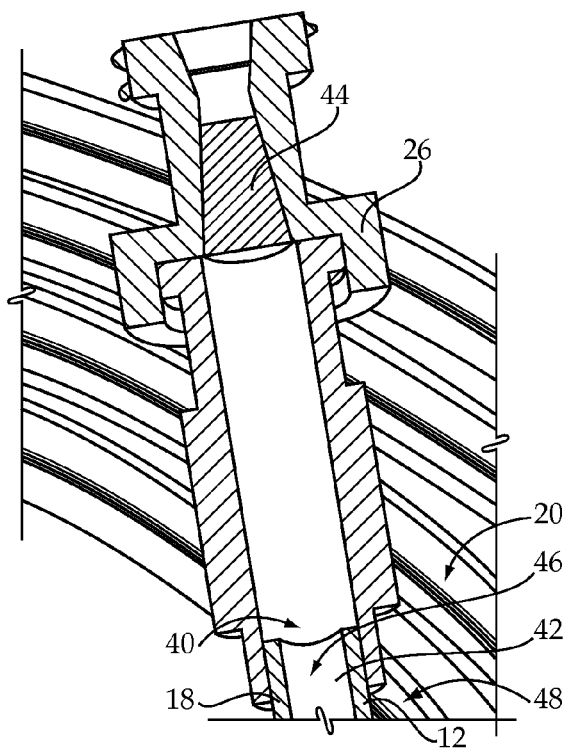
FIG. 2 is a cross sectional perspective view of the check valve of the medical lumen access device holder of FIG. 1, shown in the biased closed position, according to one aspect of the present disclosure.

Turning now to the cross sectional view of FIG. 2, the check valve 26 is shown in greater detail. According to the exemplary embodiment, a simplified version of the check valve 26 is shown positioned over a proximal opening 40 of the medical lumen access device holder 12. Although the exemplary embodiment teaches the check valve 26 positioned over the proximal opening 40, it should be appreciated that the check valve 26 may be positioned over or through any opening through the elongate tube 18, such as at a midpoint of elongate tube 18. Further, the check valve 26 may be attached to the elongate tube 18 using any known attachment means, including friction, adhesion, welding, and the like. For example, the check valve 26 may be attached over the proximal end 20 of the elongate tube 18 by adhering an internal surface of the check valve 26 to an external surface of the elongate tube 18. Alternatively, the check valve 26 may be indirectly attached to the elongate tube 18 using another fitting or device, which may, for example, facilitate a Luer lock connection.

The check valve 26 may be any type of known valve providing the functionality described herein and may be made from any suitable material, such as, for example, plastic. As shown, the elongate tube 18 defines a lumen 42 with which the check valve 26 may fluidly communicate. In particular, the check valve 26 includes a valve member 44, shown in a biased closed position in which an internal volume 46 defined by the lumen 42 is fluidly blocked from an exterior 48 of the elongate tube 18 at the proximal opening 40. As used herein, "exterior" means situated to the outside of the elongate tube 18 or, more specifically, the lumen 42. The valve member 44, as should be appreciated, may be any suitable structure comprising any suitable material for blocking flow in its closed position, which may be spring biased or otherwise biased.

Figure 3:
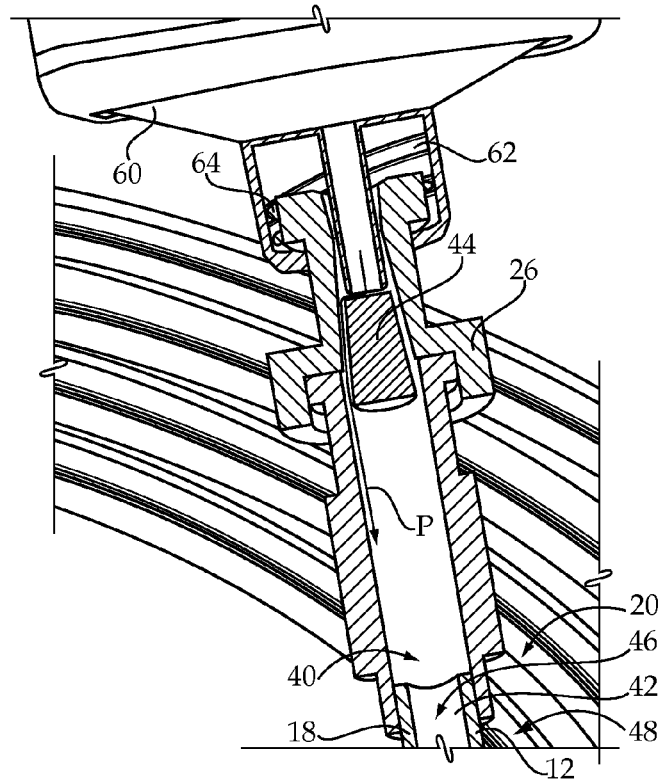
FIG. 3 is a cross sectional perspective view of the check valve of the medical lumen access device holder of FIG. 1, shown in the open position, according to another aspect of the present disclosure.

Turning now to FIG. 3, the valve member 44 is shown in an open position. In the open position, a fluid path P from the exterior 48 to the internal volume 46 is defined through the check valve 26 and more specifically, through the proximal opening 40. As should be appreciated, the open position of the valve member 44 limits flow to the direction defined by the fluid path P. According to a specific example, a syringe 60 may be attached to the check valve 26, such as by threadably engaging internal threads 62 of the syringe 60 with external threads 64 of the check valve 26. This attachment may secure attachment of the syringe 60 to the check valve 26 and may move the valve member 44 at least partially toward its open position. After the syringe 60 is securely attached, the valve member 44 may be moved to the open position by injecting a liquid 66 from the syringe 60 into the internal volume 46. Specifically, the liquid 66 may urge the valve member 44 out of its biased closed position a distance sufficient to allow the liquid 66 to flow into the lumen 42 along fluid path P.

Figure 4:
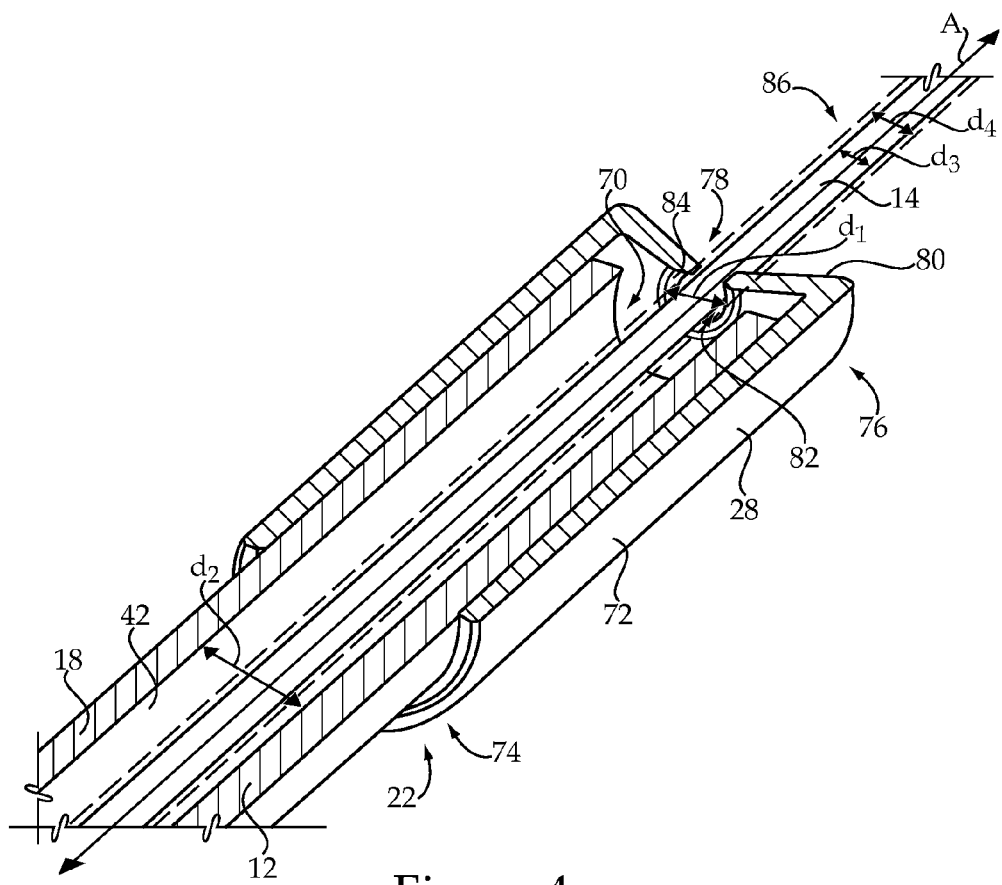
FIG. 4 is a cross sectional perspective view of the end cap of the medical lumen access device holder of FIG. 1, according to another aspect of the present disclosure.

Turning now to FIG. 4, the end cap 28, which may be optional, is shown in greater detail. The end cap 28 may be made from a plastic or other suitable material and may be attached to the elongate tube 18 using any known attachment means, including friction, adhesion, welding, and the like. According to the exemplary embodiment, the end cap 28 may be positioned over a distal opening 70 of the medical lumen access device holder 12 or, more specifically, the elongate tube 18, and may surround a portion of the external surface of the elongate tube 18. According to one example, the end cap 28 may be attached over the distal end 22 of the elongate tube 18 by adhering an internal surface of the end cap 28 to an external surface of the elongate tube 18. However, alternative configurations and attachments are contemplated.

Figure 5:
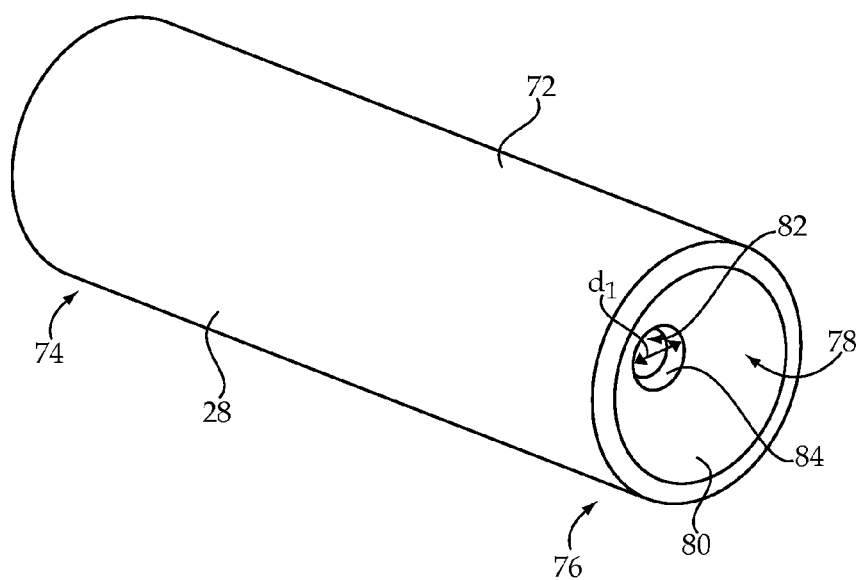
FIG. 5 is a perspective view of the end cap of the medical lumen access device holder of FIG. 1, according to another aspect of the present disclosure.

Referring also to FIG. 5, the end cap 28 may have a cylindrical body 72 having a proximal end 74 configured for attachment with the elongate tube 18 and a distal end 76 shaped to define an inwardly tapered cone-shaped channel 78. Specifically, for example, the end cap 28 may include inclined walls 80 that are tapered in the distal to proximal direction. The inwardly tapered cone-shaped channel 78, defined by the inclined walls 80, may terminate at a hole 82 having a reduced diameter $d_1$. The reduced diameter $d_1$ is smaller than a diameter $d_2$ of the lumen 42 and larger than a diameter $d_3$ of the medical lumen access device 14. Further, the reduced diameter $d_1$ is larger than a hydrated diameter $d_4$ (shown in phantom) of the medical lumen access device 14, which may be only slightly larger than the diameter $d_3$ of the medical lumen access device 14. According to some embodiments, the inwardly tapered cone-shaped channel 78 may terminate at rounded edges 84 defining the hole 82.

As shown in FIG. 4, and also in FIG. 1, the medical lumen access device 14 may be disposed at least partially within the lumen 42 and may have a proximal segment 86 extending beyond the distal opening 70. According to some embodiments, a length of the medical lumen access device 14 is greater than a length of the elongate tube 18. Lengths, as should be appreciated, may refer to axial lengths. For example, an axial length of the medical lumen access device 14 may be measured relative to an axis A of the elongate tube 18. By sizing the components as described and/or leaving the proximal segment 86 disposed outside the lumen 42, the risk of the medical lumen access device 14 becoming completely disposed within the lumen 42 and, therefore, difficult to access may be reduced.

For components that may be inserted into a patient, such as the medical lumen access device 14, "proximal" may be used to refer to the end of a component or feature that is closest to a clinician, while "distal" may be used to refer to a component or feature that is farthest away from the clinician. However, regarding the medical lumen access device 14, the proximal segment 86 may represent the end of the component that will be inserted into the patient or, alternatively, may represent the opposite end of the component that will remain outside the patient. Regarding devices that will not be inserted into a patient, such as the medical lumen access device holder 12, such references to "proximal" or "distal" may be used merely to reference and/or distinguish opposing ends.

INDUSTRIAL APPLICABILITY

The present disclosure is generally applicable to medical lumen access device holders used to store medical lumen access devices. More specifically, the present disclosure finds application with medical lumen access device holders used to store medical lumen access devices, such as, for example, wire guides or catheters, having a hydrophilic coating. Further, the present disclosure finds application in hydrating the hydrophilic coating of the medical lumen access device during storage and inhibiting leakage of the hydrating liquid from the medical lumen access device holder.

Referring generally to FIGS. 1-5, a medical lumen access device assembly 10 generally includes a medical lumen access device holder 12 and a medical lumen access device 14 having a hydrophilic coating 16. The medical lumen access device holder 12 includes an elongate tube 18 defining a lumen 42 extending from a proximal opening 40 of the elongate tube 18 to a distal opening 70 of the elongate tube 18. A check valve 26 is positioned through the proximal opening 40, or another opening, of the elongate tube 18 and includes a valve member 44 having a biased closed position wherein an internal volume 46 defined by the lumen 42 is fluidly blocked from an exterior 48 of the elongate tube 18 at the proximal opening 40 and an open position defining a fluid path P from the exterior 48 to the internal volume 46 through the proximal opening 40.

The medical lumen access device holder 12 may also include an end cap 28 attached at the distal opening 70. The end cap 28 may define an inwardly tapered cone-shaped channel 78 terminating at a hole 82 having a reduced diameter $d_1$, wherein the reduced diameter $d_1$ is smaller than a diameter $d_2$ of the lumen 42 and larger than a diameter $d_3$ of the medical lumen access device 14. As shown, the medical lumen access device 14 may be disposed at least partially within the lumen 42 and may have a proximal segment 86 extending beyond the distal opening 70. More particularly, according to the exemplary embodiment, the medical lumen access device 14 may extend through the hole 82 of the end cap 28.

As noted above, the medical lumen access device 14 may be stored, at least partially, within the medical lumen access device holder 12. For example, the medical lumen access device holder 12, along with any additional packaging, may provide protection for the medical lumen access device 14 and may ensure sterility of the medical lumen access device 14 upon delivery to an end user. Further, the medical lumen access device holder 12 may be provided in the spiral configuration shown to make the medical lumen access device holder 12, and medical lumen access device 14, more compact for shipping and storage.

Before using the medical lumen access device 14, a clinician will typically hydrate the hydrophilic coating 16 by introducing a liquid, such as saline, into the medical lumen access device holder 12. Specifically, the valve member 44 is moved from the biased closed position, as shown in FIG. 2, to the open position, as shown in FIG. 3, by injecting a liquid 66 from syringe 60 into an internal volume 46 of the medical lumen access device holder 12 through the check valve 26. This hydrates the hydrophilic coating 16, which may increase the medical lumen access device 14 to a hydrated diameter $d_4$. Once the hydrophilic coating 16 is hydrated, the medical lumen access device 14 may remain in the medical lumen access device holder 12, and oriented along a horizontal plane, until the clinician is ready to use the medical lumen access device 14. This may vary from a very short period of time to a lengthy period of time.

Leakage of the liquid 66 from the internal volume 46 to an exterior 48 is inhibited at least in part by biasing the valve member 44 from the open position (FIG. 3) to the biased closed position (FIG. 2). As should be appreciated, the check valve 26 may be positioned over any opening through the elongate tube 18, which may be positioned at any position along the axial length of the elongate tube 18, to provide a means for injecting liquid 66 into the lumen 42 and/or inhibiting leakage. Leakage of the liquid 66 may also be inhibited by reducing an effective diameter of the lumen 42, or lumen diameter $d_2$, at an end, such as the distal end 22, to a reduced diameter $d_1$. For example, the end cap 28 may be positioned over the distal opening 70 of the elongate tube 18 and may include the hole 82, which has the reduced diameter $d_1$. The reduced diameter $d_1$ may be smaller than the diameter $d_2$ of the lumen 42, but larger than both the diameter $d_3$ and hydrated diameter $d_4$ (shown in phantom) of the medical lumen access device 14.

The medical lumen access device 14, when needed, may be removed from the medical lumen access device holder 12 by grasping the proximal segment 86 of the medical lumen access device 14 and pulling the medical lumen access device 14 through the distal opening 70. As should be appreciated, if the end cap 28 is provided over the distal opening 70, the medical lumen access device 14 will be pulled through the hole 82 of the end cap 28. As shown, edges 84 defining the hole 82 may be rounded to minimize any removal of the hydrophilic coating 16 that may occur from sliding contact of the medical lumen access device 14 with the edges 84.

Friction of the medical lumen access device 14 relative to the medical lumen access device holder 12 during removal of the medical lumen access device 14 from the medical lumen access device holder 12 is reduced by biasing the valve member 44 to the biased closed position of FIG. 2, as described above. Specifically, by reducing leakage of the liquid 66 from the internal volume 46, enough of the liquid 66 may remain within the internal volume 46 to maintain hydration of the hydrophilic coating 16. If the hydrophilic coating 16 were to dehydrate, it could act as a glue between the medical lumen access device holder 12 and the medical lumen access device 14, which could make the medical lumen access device 14 stick within the medical lumen access device holder 12. This could result in damage of the medical lumen access device 14, possibly rendering the medical lumen access device 14 unusable.

After use, or when temporary storage is required, the medical lumen access device 14 may be reinserted into the medical lumen access device holder 12. Specifically, an end, such as end 86 or opposite end (not shown), of the medical lumen access device 14 may be inserted into the medical lumen access device holder 12 through the distal opening 70. As should be appreciated, if the end cap 28 is provided over the distal opening 70, the medical lumen access device 14 will be inserted through the hole 82 of the end cap 28. Such insertion may be facilitated, at least in part, by guiding the end of the medical lumen access device 14 through the inwardly tapered cone-shaped channel 78 of the end cap 28. Rounded edges 84, as described above, may minimize removal of the hydrophilic coating 16 as the medical lumen access device 14 is inserted through the hole 82.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A medical lumen access device assembly, comprising:
    a medical lumen access device holder including an elongate tube defining a lumen extending from a proximal opening of the elongate tube to a distal opening of the lumen of the elongate tube, and a check valve positioned over an opening of the elongate tube and including a valve member, wherein the valve member has a biased closed position wherein an internal volume defined by the lumen is fluidly blocked from an exterior of the elongate tube at the opening and an open position defining a fluid path from the exterior to the internal volume through the opening;
    a medical lumen access device disposed at least partially within the lumen and having a proximal segment extending beyond the distal opening, wherein at least a portion of the medical lumen access device includes a hydrophilic coating; and
    the distal opening has a diameter greater than an outer diameter of the medical lumen access device at the distal opening.

2. The medical lumen access device assembly of claim 1, further including a liquid within the internal volume in contact with the hydrophilic coating.

3. The medical lumen access device assembly of claim 2, wherein the elongate tube has a spiral configuration.

4. The medical lumen access device assembly of claim 3, further including a plurality of separators attached to the elongate tube at spaced apart axial lengths of the elongate tube.

5. The medical lumen access device assembly of claim 4, wherein the check valve is positioned over the proximal opening.

6. The medical lumen access device assembly of claim 4, wherein the medical lumen access device holder further includes an end cap positioned over the distal opening and defining an inwardly tapered cone-shaped channel terminating at a hole having a reduced diameter, wherein the reduced diameter is smaller than a diameter of the lumen and larger than a diameter of the medical lumen access device.

7. The medical lumen access device assembly of claim 6, wherein the reduced diameter is larger than a hydrated diameter of the medical lumen access device.

8. The medical lumen access device assembly of claim 7, wherein the inwardly tapered cone-shaped channel terminates at rounded edges defining the hole.

9. The medical lumen access device assembly of claim 8, wherein the check valve is positioned at the proximal opening.

10. The medical lumen access device assembly of claim 1, wherein a length of the medical lumen access device is greater than a length of the elongate tube.

11. A medical lumen access device holder, comprising:
    an elongate tube defining a lumen extending from a proximal opening of the elongate tube to a distal opening of the elongate tube;
    a check valve positioned over the proximal opening and including a valve member, wherein the valve member has a biased closed position wherein an internal volume defined by the lumen is fluidly blocked from an exterior of the elongate tube at the proximal opening and an open position defining a fluid path from the exterior to the internal volume through the proximal opening; and
    an end cap positioned over the distal opening and defining an inwardly tapered cone-shaped channel terminating at a hole having a reduced diameter, wherein the reduced diameter is smaller than a diameter of the lumen, and the inwardly tapered cone-shaped channel tapers in a distal to proximal direction.

12. The medical lumen access device holder of claim 11, wherein the elongate tube has a spiral configuration.

13. The medical lumen access device holder of claim 12, further including a plurality of separators attached to the elongate tube at spaced apart axial lengths of the elongate tube.

14. The medical lumen access device holder of claim 13, wherein the inwardly tapered cone-shaped channel terminates at rounded edges defining the hole.

15. A method of using a medical lumen access device assembly, the medical lumen access device assembly including a medical lumen access device holder including an elongate tube defining a lumen extending from a proximal opening of the elongate tube to a distal opening of the elongate tube, a check valve positioned over an opening of the elongate tube and including a valve member, wherein the valve member has a biased closed position wherein an internal volume defined by the lumen is fluidly blocked from an exterior of the elongate tube at the opening and an open position defining a fluid path from the exterior to the internal volume through the opening, an end cap positioned over the distal opening and defining an inwardly tapered cone-shaped channel terminating at a hole having a reduced diameter, wherein the reduced diameter is smaller than a diameter of the lumen, and the inwardly tapered cone-shaped channel tapers in a distal to proximal direction, and a medical lumen access device disposed at least partially within the lumen and having a proximal segment extending beyond the distal opening, wherein at least a portion of the medical lumen access device includes a hydrophilic coating, and the distal opening has a diameter greater than an outer diameter of the medical lumen access device at the distal opening, the method comprising the steps of:
    storing the medical lumen access device at least partially within the medical lumen access device holder;

moving the valve member from the biased closed position to the open position by injecting a liquid into the internal volume through the check valve;

inhibiting leakage of the liquid from the internal volume to the exterior at least in part by biasing the valve member from the open position to the biased closed position;

removing the medical lumen access device from the medical lumen access device holder through the distal opening; and reducing friction of the medical lumen access device relative to the medical lumen access device holder during the removing step with the liquid.

16. The method of claim 15, wherein injecting the liquid into the internal volume includes hydrating the hydrophilic coating.

17. The method of claim 16, further including inhibiting leakage of the liquid from the internal volume by reducing an effective diameter of the lumen at the distal end to a reduced diameter.

18. The method of claim 17, further including reinserting the medical lumen access device into the medical lumen access device holder at least in part by guiding an end of the medical lumen access device through an inwardly tapered cone-shaped channel after the removing step.

* * * * *